US012580053B2

(12) United States Patent
Jin et al.

(10) Patent No.: US 12,580,053 B2
(45) Date of Patent: Mar. 17, 2026

(54) PROTAC TARGET MOLECULE GENERATION METHOD, A COMPUTER SYSTEM, AND A STORAGE MEDIUM

(71) Applicant: Ainnocence Technologies LLC, Miami, FL (US)

(72) Inventors: Yutong Jin, Zhengzhou (CN); Siwei Li, Shanghai (CN); Junfeng Wu, Shanghai (CN); Lurong Pan, Vestavia Hill, AL (US)

(73) Assignee: Ainnocence Technologies LLC

( * ) Notice: Subject to any disclaimer, the term of this patent is extended or adjusted under 35 U.S.C. 154(b) by 922 days.

(21) Appl. No.: 17/811,333

(22) Filed: Jul. 8, 2022

(65) Prior Publication Data

US 2023/0377695 A1     Nov. 23, 2023

(51) Int. Cl.
| | |
|---|---|
| *G16C 20/50* | (2019.01) |
| *G16C 20/20* | (2019.01) |
| *G16C 20/40* | (2019.01) |
| *G16C 20/70* | (2019.01) |

(52) U.S. Cl.
CPC ............. *G16C 20/50* (2019.02); *G16C 20/20* (2019.02); *G16C 20/40* (2019.02); *G16C 20/70* (2019.02)

(58) Field of Classification Search
CPC ........ G16C 20/70; G16C 20/50; G16C 20/20; G16C 20/40
See application file for complete search history.

(56) References Cited

U.S. PATENT DOCUMENTS

| | | | |
|---|---|---|---|
| 10,622,098 B2 * | 4/2020 | Coley | G16C 20/70 |
| 11,176,462 B1 * | 11/2021 | Bastas | G06N 5/022 |
| 12,116,698 B1 | 10/2024 | Gao | |
| 2023/0019342 A1 | 1/2023 | Heath et al. | |
| 2024/0218053 A1 | 7/2024 | Binning | |
| 2024/0254179 A1 | 8/2024 | Alexander et al. | |
| 2024/0342302 A1 | 10/2024 | Jaminet et al. | |

* cited by examiner

*Primary Examiner* — An H Do
(74) *Attorney, Agent, or Firm* — Jason C. Cameron

(57) ABSTRACT

A PROTAC target molecule generation method, system, and storage medium where the method includes obtaining parameters; extract the target protein ligand structure corresponding to the first parameter in the target protein ligand database to form a first subset, extract the degradation agent fragment structure corresponding to the parameter in the degradation agent fragment database to form a second subset, and extract the linker fragment structure corresponding to the parameter in the linker fragment database to form a third subset; permute and combine each fragment structure in the subsets to generate PROTAC target molecules. The extract required fragment structures from various databases, then permute and combine the three groups of fragment structure, and use big data and computational processing to be used for experiments, avoids the omission of the combination of structural fragments, improves the accuracy of molecular design and speeds up drug research and development processes.

10 Claims, 3 Drawing Sheets

100

AUTOMATICALLY IDENTIFY THE PROTEIN STRUCTURE OR PROTAC MOLECULE — INPUT

EXTRACT TARGET PROTEIN LIGAND STRUCTURE, THE DEGRADATION AGENT FRAGMENT STRUCTURE, AND THE LINKER FRAGMENT STRUCTURE FROM DATABASE OR BY AI MODEL — S1

PERMUTE AND COMBINE ALL THE FRAGMENT STRUCTURES — S2

OUTPUT PROTAC TARGET MOLECULE — S3

USE AI SCORE MODEL TO ORDER PROTAC TARGET MOLECULE — S4

OUTPUT THE OPTIMAL DATA — S5

100

300

PROTAC TARGET MOLECULE GENERATION METHOD, A COMPUTER SYSTEM, AND A STORAGE MEDIUM

CROSS-REFERENCE TO RELATED APPLICATIONS

This Application claims priority from a patent application filed in China having Patent Application No. 2022105370160 filed on May 17, 2022, and titled "A PROTAC TARGET MOLECULE GENERATION METHOD, A COMPUTER SYSTEM, AND A STORAGE MEDIUM".

FIELD OF INVENTION

The present specification relates to the field of computer-aided drug molecule design, in particular to a proteolysis-targeting chimera (PROTAC) target molecule generation method, a computer system, and a storage medium.

BACKGROUND

PROTAC is a hybrid bifunctional small molecule compound with two functional fragment of its structure, one is the target protein ligand structure that binds to the target protein in the cell, and the other is the degradation agent fragments that binds to ligand structure of E3 ubiquitin. The functional fragments are bounden by a Linker fragment to form a multi-fragment small molecular structure. Compared with traditional targeted therapy, PROTAC molecule has many therapeutic advantages. In recent years, drug research and development companies have invested in drug screening research of PROTAC molecule.

The current design of PROTAC molecules still depends on the experience of researchers and literature review, and the design speed is slow and occupies a lot of energy of researchers, which affects the development of downstream experiments. With the development of PROTAC technology, new PROTAC molecular data and structural data appear constantly, and the number of data increases rapidly. Traditional molecular design methods cannot adapt to massive data structures, a large number of structural data and molecular data are not effectively utilized, and there is a lack of big data-driven PROTAC molecular generation methods.

SUMMARY

In view of the problems existing in the prior art, the purpose of the present invention is to provide a PROTAC target molecule generation method, a computer system and a storage medium, wherein the PROTAC target molecule generation method can speed up the design speed of PROTAC molecules, thereby speed up the drug research and development process.

The embodiment of this specification provides the following technical solutions.

A PROTAC target molecules generation method includes the following steps:

obtain a first parameter, a second parameter and a third parameter, extract a target protein ligand structure corresponding to the first parameter in a target protein ligand database to form a first subset, extract the degradation agent fragment structure corresponding to the second parameter in the degradation agent fragment database to form a second subset, extract the linker fragment structure corresponding to the third parameter in the linker fragment database to form a third subset; permute and combine the fragment structures in the first subset, the second subset and the third subset to generate PROTAC target molecules.

Through the above method, the target protein ligand structure, extract and output the a target protein ligand structure, the degradation agent fragment structure and the linker fragment structure which meet the requirements from the target protein ligand database, the degradation agent fragment database and the linker fragment database respectively, through the first parameter, the second parameter and the third parameter transmitted or defaulted by the user, and then the three groups of fragment structures are permuted and combined, and PROTAC target molecules are quickly and efficiently generated by using big data and computational processing, so as to be used in subsequent experiments, avoid structural fragments, improving the accuracy of molecular design, and speeding up the whole drug research and development process.

The present invention also provides a solution, extract the target protein ligand structure corresponding to the first parameter in the target protein ligand database to form the first subset, including: obtain the ligand characteristic structure in the target protein ligand structure input by the user, compare the similarity between each target protein ligand structure in the target protein ligand database and the ligand characteristic structure, and output the target protein ligand structure corresponding to the first parameter with the highest similarity degree to form the first subset;

and/or, extract the degradation agent fragment structure corresponding to the second parameter in the degradation agent fragment database to form a second subset; including: obtain the degradation agent characteristic structure of the degradation agent fragment structure input by the users, compare the similarity between each degradation agent fragment in the degradation agent fragment database with the degradation agent characteristic structure, output the degradation agent fragment structure corresponding to the second parameter with the highest similarity degree to form the second subset.

The present invention also provides another solution, extract the target protein ligand structure corresponding to the first parameter in the target protein ligand database to form the first subset, including: the target protein ligand structures in the target protein ligand database are arranged in descending order according to the activity order, and output the target protein ligand structure corresponding to the first parameter to form the first subset;

and/or, extract the degradation agent fragment structure corresponding to the second parameter in the degradation agent fragment database to form the second subset including: the degradation agent fragment structures in the degradation agent fragment database are arranged in descending order according to the activity order, and output the degradation agent fragment structure corresponding to the second parameter to form the second subset.

The present invention also provides another solution, extract the linker fragment structure corresponding to the third parameter in the linker fragment database to form the third subset, including:

perform the length search in the linker fragment database, and output the linker fragment structure conforming to the preset length to form the third subset.

The present invention also provides another solution, the preset length is an integer.

The present invention also provides another solution, the length search comprises the following steps:

obtain the first PROTAC molecule;

remove the active fragment structure and the degradation agent fragment structure in the first PROTAC molecule to obtain an intermediate molecule;

convert the intermediate molecule into a graph structure, and calculate the length between two vertices in the graph structure, wherein the graph structure comprises atoms and line segments binding the adjacent atoms.

The present invention also provides another solution, before obtaining the first parameter, the second parameter, and the third parameter, the method for generating the PROTAC target molecule further comprises:

obtain the second PROTAC molecule input by the user, wherein the second PROTAC molecule is expressed by the simplified molecular-input line-entry system (SMILES) molecular structure or the PDB protein structure.

The present invention also provides another solution, after generating the PROTAC target molecule, the method for generating the PROTAC target molecule further comprises:

score the PROTAC target molecule according to a preset scoring model, and derive the PROTAC target molecule with a score greater than or equal to a first threshold.

The present invention also provides another solution, the preset scoring model comprises a binary classification model using a random forest method.

The present invention also provides another solution, the fragment structure in at least one of the target protein ligand database, the degradation agent fragment database, and the linker fragment database is from an open source database, and the open source databases includes but not limited to at least one of PROTAC-DB, PROTACpedia, Chembl, and BindingDB.

The present invention also provides a computer system, which includes a memory, a processor, and a computer program stored in the memory and running on the processor. When the processor executes the computer program, it realizes the steps of the PROTAC target molecule generation method as described in any one of the foregoing.

The present invention also provides a computer-readable storage medium, on which a computer program is stored, and when the computer program is executed by a processor, it realizes the steps of the PROTAC target molecule generation method as described in any one of the foregoing.

Compared with the prior art, the beneficial effects achieved by the above-mentioned at least one technical solution adopted in the embodiment of this specification include at least the following: through the above-mentioned method, permute and combine the active fragment structure, the degrading agent fragment structure and the linker fragment structure, accelerate the generation speed of the virtual PROTAC target molecule and the design speed of the PROTAC molecule by taking advantage of the big data of each database and the operation processing of computer or cloud computing, avoid the combination omission of structural fragments, improve the precision of molecular design, and liberate researchers from the complicated work of molecular design, and better concentrate on downstream experiments, pharmacological research and other work, thus improve the overall efficiency of pharmaceutical research and development and speed up the process of pharmaceutical research and development.

BRIEF DESCRIPTION OF THE DRAWINGS

In order to illustrate the technical solutions of the embodiments of the present application more clearly, the following briefly introduces the drawings that are used in the embodiments. Obviously, the drawings in the following description are only some embodiments of the present application, and for persons skilled in the art, other drawings may also be obtained according to the drawings without any creative efforts.

DETAILED DESCRIPTION OF THE DISCLOSURE

Figure 1:
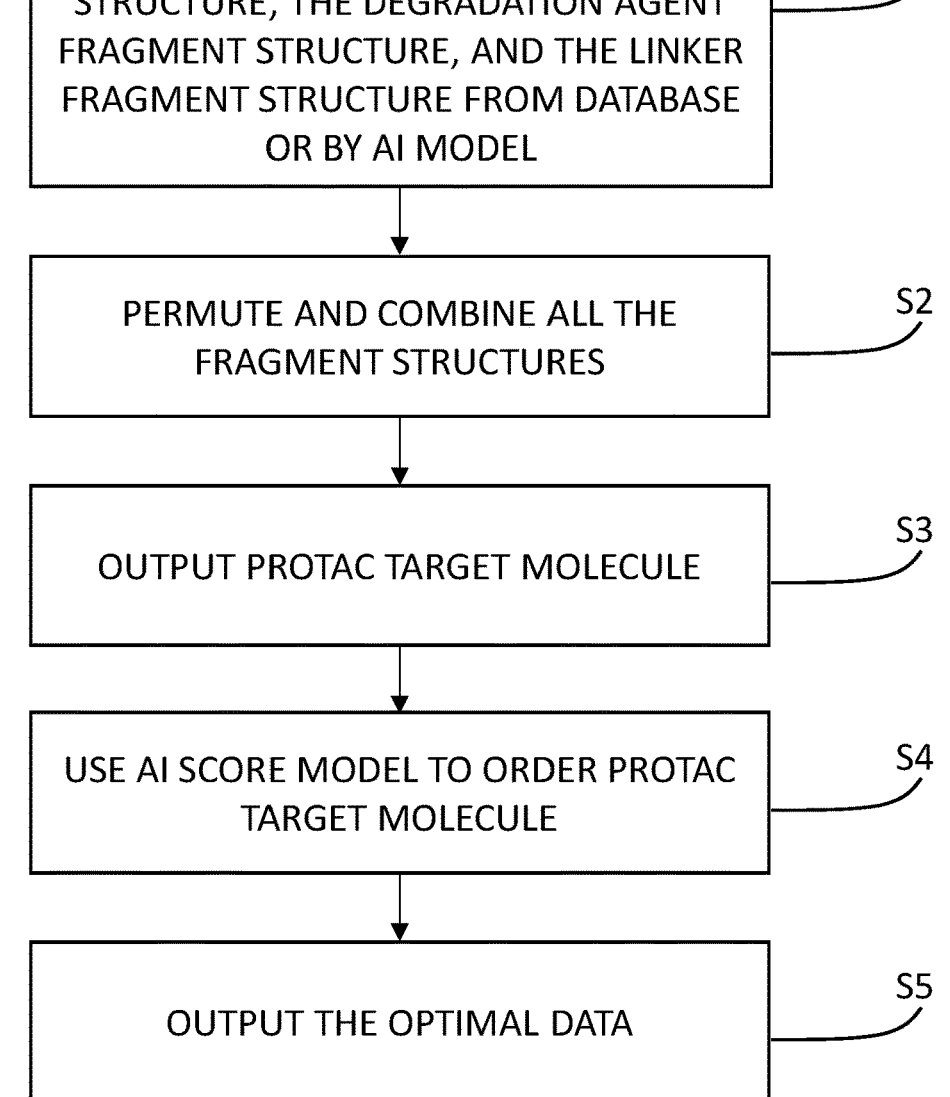
FIG. 1 is a flowchart of a PROTAC target molecule generation method.

The embodiments of that present application are described in detail below with reference to the drawings.

The embodiments of the present application are described below by way of specific examples, and those skilled in the art can easily understand other advantages and effects of the present application from the contents disclosed in this specification. Obviously, the described embodiments are only a part of the embodiments of the present application, but not all of the embodiments. The present application may be implemented or applied by different other embodiment, and that details of the present specification may be modified or changed from various aspect and applications without departing from the spirit of the present application. It should be noted that the following embodiments and the features in the embodiments can be combined with each other without conflict. Based on the embodiments in the present application, all other embodiments obtained by persons of ordinary skill in the art without creative work are within the scope of the protection of the present application.

It should be noted that various aspects of embodiments within the scope of the appended claims are described below. It should be apparent that the aspects described herein may be embodied in a wide variety of forms, and that any specific structures and/or functions described herein are merely illustrative. Based on the present application, persons skilled in the art will appreciate that one aspect described herein may be implemented independently of any other aspect and that two or more of these aspects may be combined in various ways. For example, any number and aspects set forth herein may be used to implement an apparatus and/or practice a method. In addition, the apparatus may be implemented and/or the method practiced using other structures and/or functionalities in addition to one or more of the aspects set forth herein.

It should also be noted that the illustrations provided in the following examples illustrate the basic concepts of the present application by way of illustration only. The drawings only show the components related to the present application and are not drawn according to the number, shape and size of the components in the actual implementation. The type, number and proportion of each component in the actual implementation may be changed at will, and the layout type of the components may be more complicated.

In addition, in the description of this specification, it is to be understood that the directional words such as "upper", "lower", "inner", and the numerical words such as "outer", and "first", "second", "third", described in the exemplary embodiments of this specification, are described in terms of the drawings, and should not be understood as limiting the exemplary embodiments of this specification.

In addition, in the following description, specific details are provided to facilitate a thorough understanding of the examples. However, persons skilled in the art will understand that the described aspects may be practiced without these specific details.

PROTAC is a hybrid bifunctional small molecule compound with a functional fragment at both ends of its structure, one is the target protein ligand structure that binds to the target protein in the cell, and the other is the degradation agent fragments that binds to ligand structure of E3 ubiquitin. The two functional fragments are bounden by a Linker fragment to form a small molecular structure of "target protein ligand-linker-degradation". The ubiquitination tag is added to the target protein by E3 ligase, which initiates a powerful ubiquitination hydrolysis process in the cell and specifically degrades the target protein through the ubiquitin-protease pathway. Compared with traditional targeted therapy, PROTAC molecules have many therapeutic advantages. In recent years, drug research and development companies have invested in the research of drug screening of PROTAC molecules.

Drug screening is an important way to discover drug lead compounds, and a good molecular library is a shortcut to drug screening. However, the current design of PROTAC, molecular structure is still in the stage of reading literature and tree hand designing, relying heavily on the experience of researchers and literature reports. The design speed of molecules is slow, which takes up a lot of researchers' energy and affects the development of downstream experiments, and does not involve the design method of using databases and computer-aided algorithms. With the development of PROTAC technology, new PROTAC molecular data and structural data appear constantly, and the number of data increases rapidly. Traditional molecular design methods cannot adapt to massive data structures, a large amount of structural data and molecular data are not effectively utilized, and there is a lack of big data-driven PROTAC molecular generation methods.

Therefore, the inventor proposed a solution, which reasonably utilized the data in PROTAC molecular structure database and used the preset algorithm to generate PROTAC target molecules. Due to the triblock structure of PROTAC molecule, the preferred target protein ligand structure, linker fragment structure and degradation agent fragment structure were screened by artificial intelligence search or optimization from the database, and then these fragments constitute the PROTAC target molecule by the way of permutation and combination, to form PROTAC molecule of guiding the downstream experiment. This method utilizes the existing molecular structure database, combined with the computing power of the computer, to efficiently generate PROTAC target molecules, which can speed up the research and development of PROTAC drugs, and solve the problems of slow design speed of PROTAC target molecules, and dependence on personnel experience and literature search.

The technical solutions provided by various embodiments of this application will be explained with reference to the following drawings.

The invention provides a PROTAC target molecule generating method, which comprises that following steps:

Step 1, obtain a first parameter, a second parameter and a third parameter, and respectively extract molecular fragments corresponding to the first parameter, the second parameter and the third parameter from three databases. Specifically, the three databased are respectively the three databases corresponding to the small molecular structure of PROTAC, namely, target protein ligand database, degradation agent fragment database and linker fragment database. In each database, do the following:

extract the target protein ligand structure corresponding to the first parameter in a target protein ligand database to form a first subset;

extract the degradation agent fragment structure corresponding to the second parameter in the degradation agent fragment database to form a second subset;

extract the linker fragment structure corresponding to the third parameter in the linker fragment database to form a third subset.

Step 2, permute and combine the fragment structures in the first subset, the second subset and the third subset to generate PROTAC target molecules.

It should be noted that in the process of permutation and combination, the target protein ligand structure and the degradation agent fragment structure can be combined at both ends of the linker fragment structure to generate PROTAC target molecules with the standard structure of "target protein ligand—Linker—degradation agent"; it is also possible to combine only the ligand structure of the target protein with the linker fragment structure, or combine only the degradation agent fragment structure with the linker fragment structure, to generate PROTAC target molecules with non-standard structure.

It should also be noted that the length of the linker fragment structure can be "0", at this time, the combined PROTAC target molecule only contains the target protein ligand structure and the degradation agent fragment structure.

It should also be noted that anyone or combination of the first parameter, the second parameter and the third parameter can be parameters input by the user; It can also be a preset parameter in the system. When there is no parameter input by the users, the molecular generation method calls the preset parameter to perform the operation.

Through the above method, the computer directly obtains the corresponding number from the corresponding molecular fragment database according to the first parameter, the second parameter and the third parameter, and then combines each fragment in a permutation and combination way to form PROTAC target molecules which can be used for downstream experimental research, with little dependence on personnel experience and literature reports. Through the processing ability of big data and computer algorithms, and the number of each molecular fragment can be obtained by adjustment, generate a corresponding number of target molecules, for example, if the first parameter is set to N, the second parameter is E, and the third parameter is L, the number of PROTAC target molecules generated will be N×E×L, which is high in efficiency, and there will be no human omission, and there will be no omission of any specified structural fragment due to the problems of personnel experience or whether the literature has reported, so the structural integrity of the generated target molecule data is good. Through the above method, PROTAC target molecules can be efficiently formed, which is beneficial to liberate researchers and make them pay more attention to downstream experiments, pharmacology, kinetics and other aspects of research, rather than a large number of literature search and molecular structure design, and accelerate the research and development progress.

Figure 2:
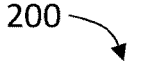
FIG. 2 is a structure block diagram of a computing system for generating PROTAC target molecules.
Figure 2:
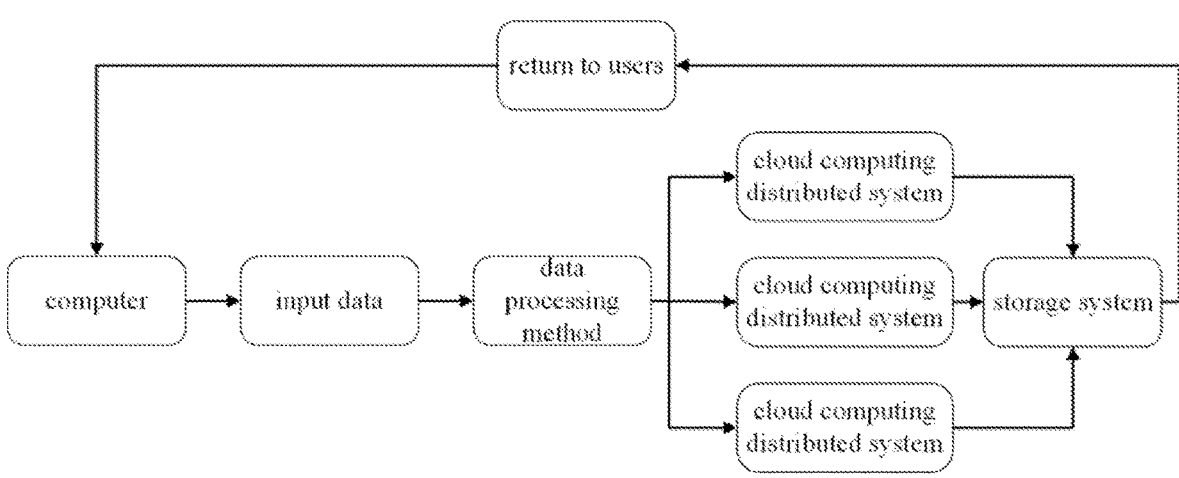

Specifically, as shown in the flowchart 100 FIG. 1 and flowchart 200 of FIG. 2, a user inputs data through a computer, and any one or any combination of the first parameter, the second parameter, and the third parameter of these data packets, if one or some parameters are not input by the user, directly invoke the pre-stored data. Local computers or a plurality of computers in a cloud computing distribution system, extract the target protein ligand structure corresponding to the first parameter from the target protein ligand database according to the above parameters, and output the first subset, extract the degradation agent fragment structure corresponding to the second parameter from the degradation agent fragment database, and output the second subset; extract the linker fragment structure corresponding to the third parameter from the linker fragment database, and output the third subset. It should be noted that the extraction of any ligand structure or fragment structure can be performed by one computer or several computers distributed in the cloud network. Then, each subset is permuted and combined, for example, N target protein ligand structures are extracted from the target protein ligand database, E degradation agent fragment structures are extracted from the degradation agent fragment database, and L linker fragment structures are extracted from the linker fragment database, through premutation and combination, a three-dimensional matrix of the number of N×E×L target molecules is generated, and after these target molecules are stored, such as CSV or Excel format data, will be returned to users for subsequent experimental research.

In some embodiments, the target protein ligand structure can be extracted from the target protein ligand database to obtain the first subset by similarity comparing. Specifically, obtain the ligand characteristic structure in the target protein ligand structure input by the user, and then invoke a preset comparison algorithm, compare the similarity between each target protein ligand structure in the target protein ligand database and the ligand characteristic structure, and then the target protein ligand structures in the database are arranged in descending order according to the similarity degree, and output the target protein ligand structures of the first parameter quantity to form the first subset.

It should be noted that the user can define the starting position of the output data by himself or by a preset way, such as starting from the first one in descending order or starting from the nth one in descending order.

It should also be noted that users can use the SMILES compound sequence structure or PDB protein structure to express the input target protein ligand structure.

In other embodiments, after similarity comparing of each target protein ligand structure in the target protein ligand database with the ligand characteristic structure, score each target protein ligand structure according to the similarity degree, and then output the target protein ligand structure with the score higher than a preset value (such as 0.7) to form the first subset.

In some embodiments, the structure of degradation agent fragments can be extracted from the database of degradation agent fragments to obtain a second subset by similarity comparing. Specifically, obtain the degradation agent characteristic structure of the degradation agent fragment structure input by the users, and then invoke a preset comparison algorithm, compare the similarity between each degradation agent fragment in the degradation agent fragment database with the degradation agent characteristic structure, and then degradation agent fragments in the database are arranged in descending order according to the similarity degree, and output degradation agent fragments with a second parameter quantity to form a second subset.

Similarly, the user can define the starting position of the output data by user-defined or preset method; Users can use the sequence structure of SMILES compound to express the fragment structure of degradation agent; output the degradation agent fragment structure higher than the preset value in the way of similarity scoring, which is not repeated here.

In some embodiments, the target protein ligand structure can be extracted from the target protein ligand database to obtain the first subset by activity ordering. Specifically, the target protein ligand structures in the target protein ligand database are arranged in descending order according to the order of chemical activity or pharmacological activity, and output the target protein ligand structures of the first parameter number to form a first subset.

In other embodiments, preset an activity scoring algorithm in the computer, and invoke the activity scoring algorithm to score each target protein ligand structure according to the chemical activity or pharmacological activity, and then output the target protein ligand structure with the score higher than a preset value (such as 0.7) to form the first subset.

In some embodiments, the degradation agent fragments structure can be extracted from the degradation agent fragments database to obtain the second subset by activity ordering. Specifically, the degradation agent fragment structures in the degradation agent fragment database are arranged in descending order according to the order of chemical activity or pharmacological activity, and a second parameter quantity of degradation agent fragment structures are output to form a second subset.

Similarly, can output the degradation agent fragment structure higher than the preset value by scoring the chemical activity or pharmacological activity, which will not be repeated here.

In some embodiments, perform the length search in the linker fragment database, and output the linker fragment structure conforming to the preset length to form the third subset.

Preferably, the preset length is an integer.

It should be noted that the length calculation of linker fragment structure can use SMILES compound sequence structure to express linker fragment structure, and can also use graphic structure to express linker fragment structure. The graphic structure includes atoms and line segments binding adjacent atoms, and the length of linker fragment structure refers to the distance between atoms located at both ends.

By searching the linker fragment structure whose length accords with the preset length in the linker fragment database, a group of PROTAC target molecules with similar distances between the target protein ligand structure and the degradation fragment can be formed, which is beneficial to the similarity research.

In some embodiments, performing the length search in the linker fragment database, further comprises the following steps:

Step S1, obtain the first PROTAC molecule.

It should be noted that the first PROTAC molecule can be obtained by user input or invoking data.

Step S2, remove the active fragment structure and the degradation agent fragment structure in the first PROTAC molecule to obtain an intermediate molecule.

It should be noted that, due to the small molecular structure of "target protein ligand -Linker-degrading agent" unique to PROTAC molecule, when using SMILES compound sequence structure or PDB protein structure to express PROTAC molecule, we can identify the target protein ligand structure, linker fragment structure and degradation agent fragment structure by identifying special node markers, and then refer to the node marks to remove the active fragment structure and degradation agent fragment structure, so as to obtain intermediate molecules containing linker fragment structure.

Step S3, convert the intermediate molecule into a graph structure and calculate the length between two vertices in the graph structure, wherein the graph structure comprises atoms and line segments binding the adjacent atoms.

In some embodiments, before obtaining the first parameter, the second parameter, and the third parameter, the method for generating the PROTAC target molecule further comprises: obtain the second PROTAC molecule input by the user, wherein the second PROTAC molecule is expressed by the SMILES molecular structure or the PDB protein structure. The obtained second PROTAC molecule is used to extract the ligand characteristic structure of the target protein ligand structure and/or the degradation agent characteristic structure of the degradation agent fragment structure.

In some embodiments, after generating the PROTAC target molecule, the method for generating the PROTAC target molecule further comprises: step S4 score the PROTAC target molecule according to a preset scoring model, and step S5 derive the PROTAC target molecule with a score greater than or equal to a first threshold.

Figure 3:
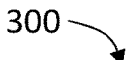
FIG. 3 is a flowchart of an AI scoring method.
Figure 3:
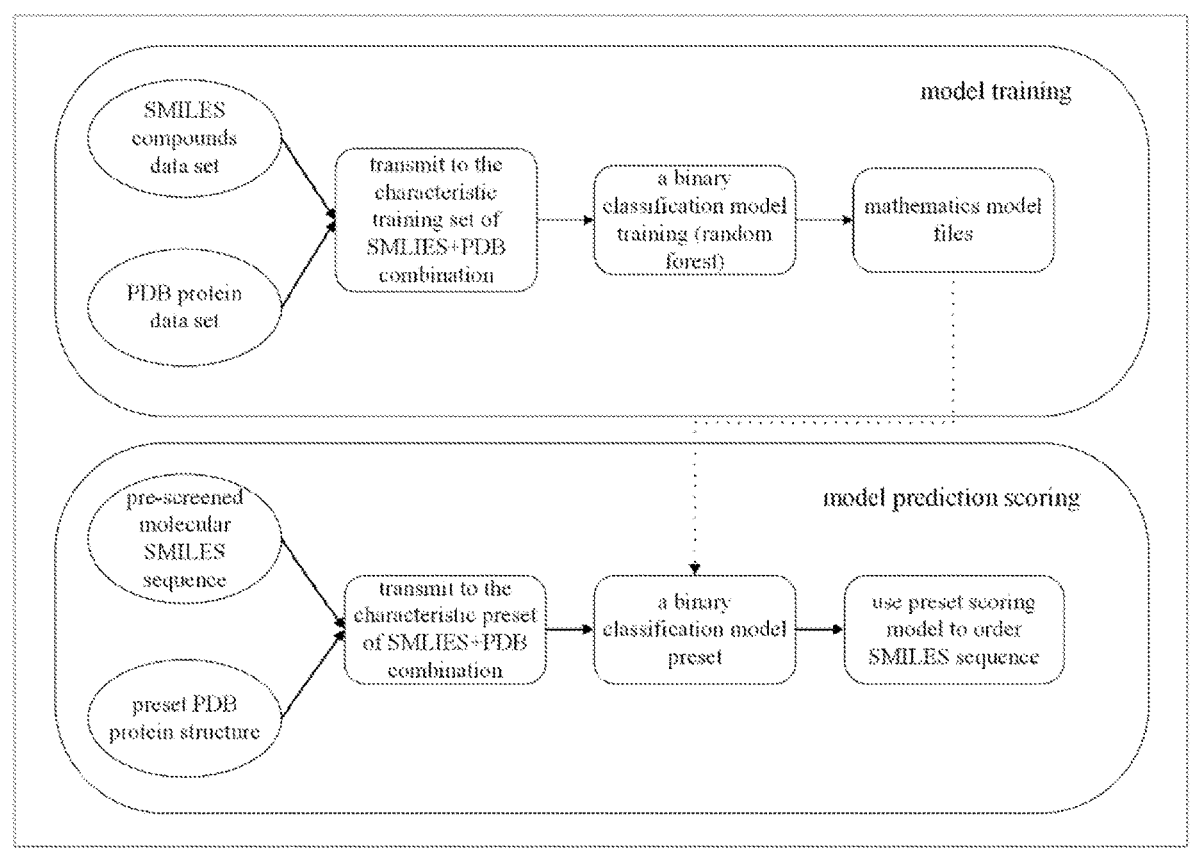

Specifically, as shown in FIG. 3, the flowchart 300 shows the preset scoring model to include:

Model training module: PDB protein data set and ligand small molecule data set integrated by open source data, train the above two data sets by machine learning algorithms such as random forest and SVM (not shown in the figure), and output available mathematical model files. Among them, PDB protein data is text data, and ligand small molecule data is SMILES compound sequence data.

Model prediction scoring module: input the pre-screened molecular SMILES sequence (PROTAC target molecule) and the preset protein text structure into the trained mathematical model file, output the probability score of the machine learning model as the weight of generating rules, and order the pre-screened molecular SMILES sequence by using the preset scoring model. Finally, according to the amount of data required by users, output in whole or in part a certain number of ordered pre-screened molecular SMILES sequences.

In some embodiments, the fragment structure in at least one of the target protein ligand database, the degradation agent fragment database, and the linker fragment database is from an open source database, the open source database includes but not limited to at least one of PROTAC-DB, PROTACpedia, Chembl, and BindingDB. Wherein, the fragment structure refers to target protein ligand structure in target protein ligand database, the degradation agent fragment structure in degradation agent fragment database and the linker fragment structure in linker fragment database.

Example 1

Input PDB protein structure:

use AI model, order target protein ligand structures in target protein ligand database, output N target protein ligand structures, order the degradation agent fragment structures in degradation agent fragment database, output E degradation agent fragment structures, and invoke L linker fragment structures from linker fragment database, wherein linker fragment structures contain fragments with different lengths; permute and combine the data of target protein ligand structure, degradation agent fragment structure and linker fragment structure to output N×E×L compounds;

through AI model, score and order according to activity or pharmacological properties;

output the data set of PROTAC target molecules.

Example 2

Input the SMILES compound sequence;

Carry out similarity search, output N target protein ligand structures with the highest similarity from the target protein ligand database, output E degradation agent fragment structures with the highest similarity degree from the degradation agent fragment database, automatically identify the Linker length by the SMILES sequence, and output the L linker fragment structures conforming to the preset length from the linker fragment database based on preset parameters;

permute and combine the data of the target protein ligand structure, the degradation agent fragment structure and the linker fragment structure, and output N×E×L compounds;

through AI model, score and order according to pharmacological properties;

output the data set of PROTAC target molecules.

Example 3

Input the SMILES compound sequence;

carry out similarity search, output N target protein ligand structures with the highest similarity from the target protein ligand database, output E degradation agent fragment structures with the highest similarity degree from the degradation agent fragment database, wherein the degradation agent fragment database also contains autophagy-related micro molecule fragments and K60 polymorphism, two degradation active fragments. The output degradation agent fragment structure also contains autophagy-related micro molecule fragments and K60 polyubiquitination degradation active fragments, automatically identify the Linker length by the SMILES sequence, and output the L linker fragment structures conforming to the preset length from the linker fragment database based on preset parameters, permute and combine the data of the target protein ligand structure, the degradation agent fragment structure and the linker fragment structure, and output N×E×L compounds;

through AI model, score and order according to pharmacological properties;

output the data set of the AUTAC/ATTEC compounds.

Example 4

Output the SMILES compound sequence;

carry out similarity search, output N target protein ligand structures with the highest similarity from the target protein ligand database, output E degradation agent fragment structures with the highest similarity degree from the degradation agent fragment database without using the linker fragment database;

permute and combine the data of the target protein ligand structure and degradation agent fragment structure to output N×E compounds;

the data are permuted and combined to output N*E compounds;

score and order through AI model;

output the data set of the target molecular glue compounds.

Example 5

Input a first PDB protein structure and a second PDB protein structure;

carry out similarity search, the target protein ligand database outputs N1 target protein ligand structures with the highest similarity with the first PDB protein structure, and outputs N2 target protein ligand structures with the highest similarity with the second PDB protein structure;

permute and combine N1 target protein ligand structures and N2 target protein ligand structures, and output N1×N2 compounds;

through AI model, score and order according to pharmacological properties;

output the data set of the target molecular glue compounds.

Example 6

Input a first PDB protein structure and a second PDB protein structure;

carry out similarity search, the target protein ligand database outputs N1 target protein ligand structures with the highest similarity with the first PDB protein structure, and outputs N2 target protein ligand structures with the highest similarity with the second PDB protein structure, and in addition, invoke L linker fragment structures from linker fragment database, wherein linker fragment structures contain fragments with different lengths;

permute and combine N1 target protein ligand structures, N2 target protein ligand structures and L linker fragment structures, and output N1×N2×L compounds;

through AI model, score and order according to pharmacological properties;

output the data set of the target molecular glue compounds.

Based on the same inventive idea, the embodiment of this specification also provides a computer system, which includes a memory, a processor, and a computer program stored in the memory and running on the processor. When the processor executes the computer program, it realizes the steps of the PROTAC target molecule generation method as described in any one of the foregoing.

The technical effects brought by the computer system provided by the above embodiments can refer to the technical effects provided by the above embodiments of PROTAC target molecule generation method, which will not be repeated here.

Based on the same inventive idea, the embodiment of this specification also provides a computer readable storage medium, on which a computer program is stored, and when the computer program is executed by a processor, it realizes the steps of the PROTAC target molecule generation method as described in any one of the foregoing.

The technical effects brought by the computer readable storage media provided by the above embodiments can refer to the technical effects provided by the above embodiments of the PROTAC target molecule generation method, which will not be repeated here.

Each embodiment in this specification is described in a progressive way, and the same and similar parts between the various embodiments may be referred to each other, and each embodiment emphasizes to describe the differences from other embodiments. In particular, for the method embodiments described later, since they correspond to the system, the description is relatively simple, and related parts refer to the partial descriptions of the system embodiments.

The embodiments described herein are only specific embodiments of the present application, and are not intended to limit the protection scope of the present application. Any modification or equivalent that can be easily conceived by persons skilled in the art should all fall within the protection scope of the present application. Therefore, the protection scope of the present disclosure is subject to the protection scope of the claims.

The invention claimed is:

1. A proteolysis-targeting chimera (PROTAC) target molecule generation method, characterized by comprising the following steps:

obtaining a first parameter, a second parameter and a third parameter;

extracting a target protein ligand structure corresponding to the first parameter in a target protein ligand database to form a first subset;

extracting a degradation agent fragment structure corresponding to the second parameter in a degradation agent fragment database to form a second subset;

extracting a linker fragment structure corresponding to the third parameter in a linker fragment database to form a third subset, wherein extracting the linker fragment structure includes performing a length search in the linker fragment database to output a linker fragment structure conforming to a preset length to form the third subset; and permuting and combining the fragment structures in the first subset, the second subset, and the third subset to generate one or more PROTAC target molecules, wherein the length search comprises:

obtaining a first PROTAC molecule;

identifying special node markers in the first PROTAC molecule;

removing an active fragment structure and the degradation agent fragment structure in the first PROTAC molecule based on the special node markers to obtain an intermediate molecule to obtain an intermediate molecule; and converting the intermediate molecule into a graph structure and calculating a length between two vertices in the graph structure, wherein the graph structure comprises atoms and line segments binding adjacent atoms.

2. The PROTAC target molecule generation method according to claim 1, wherein extracting the target protein ligand structure corresponding to the first parameter in the target protein ligand database to form the first subset includes:

obtaining a ligand characteristic structure in a target protein ligand structure input by a user;

comparing a similarity between each target protein ligand structure in the target protein ligand database and the ligand characteristic structure; and outputting the target protein ligand structure corresponding to the first parameter with the highest similarity degree to form the first subset; and wherein

13

14 extracting a degradation agent fragment structure corresponding to the second parameter in the degradation agent fragment database to form a second subset includes:

obtaining a degradation agent characteristic structure of the degradation agent fragment structure input by the user, comparing a similarity between each degradation agent fragment in the degradation agent fragment database with the degradation agent characteristic structure, and outputting the degradation agent fragment structure corresponding to the second parameter with the highest similarity degree to form the second subset.

3. The PROTAC target molecule generation method according to claim 1, wherein extracting the target protein ligand structure corresponding to the first parameter in the target protein ligand database to form the first subset includes:

arranging the target protein ligand structures in the target protein ligand database in descending order according to a first activity order; and outputting the target protein ligand structure corresponding to the first parameter to form the first subset, and wherein extracting the degradation agent fragment structure corresponding to the second parameter in tire degradation agent fragment database to form the second subset includes:

arranging the degradation agent fragment structures in the degradation agent fragment database in descending order according to a second activity order; and outputting the degradation agent fragment structure corresponding to the second parameter to form the second subset.

4. The PROTAC target molecule generation method according to claim 1, wherein the preset length is an integer.

5. The PROTAC target molecule generation method according to claim 1, characterized in that before obtaining the first parameter, the second parameter, and the third parameter, the method for generating the PROTAC target molecule further comprises:

obtaining a second PROTAC molecule input by the user, wherein the second PROTAC molecule is expressed by a simplified molecular-input line-entry system (SMILES) molecular structure or a Protein Data Bank (PDB) protein structure.

6. The PROTAC target molecule generation method according to claim 1, wherein after generating the PROTAC target molecule, the method for generating the PROTAC target molecule further comprises:

scoring the PROTAC target molecule according to a preset scoring model; and deriving the PROTAC target molecule with a score greater than or equal to a first threshold.

7. The PROTAC target molecule generation method according to claim 6, characterized in that the preset scoring model comprises a binary classification model using a random forest method.

8. The PROTAC target molecule generation method according to claim 1, wherein the fragment structure in at least one element of a set comprising the target protein ligand database, the degradation agent fragment database, and the linker fragment database is from an open source database; and wherein the open source database includes, but is not limited to, at least one element of a set comprising PROTAC-DB, PROTACpedia, Chembl, and BindmgDB.

9. A computer system comprising a memory, a processor, and a computer program stored in the memory and running on the processor, characterized in that when the processor executes the computer program, realizes the steps of a proteolysis-targeting chimera (PROTAC) target molecule generation method according to claim 1.

10. A computer-readable storage medium, on which a computer program is stored, characterized in that when the computer program is executed by a processor, realize the steps of a proteolysis-targeting chimera (PROTAC) target molecule generation method according to claim 1.

* * * * *